United States Patent [19]

Hefner, Jr. et al.

[11] Patent Number: 5,262,509
[45] Date of Patent: Nov. 16, 1993

[54] MESOGENIC GLYCIDYL AMINES

[75] Inventors: Robert E. Hefner, Jr.; Jimmy D. Earls, both of Lake Jackson, Tex.

[73] Assignee: The Dow Chemical Company, Midland, Mich.

[21] Appl. No.: 890,734

[22] Filed: May 28, 1992

Related U.S. Application Data

[63] Continuation-in-part of Ser. No. 663,499, Mar. 1, 1991, abandoned, which is a continuation-in-part of Ser. No. 562,289, Aug. 3, 1990.

[51] Int. Cl.[5] .............................................. C08G 65/08
[52] U.S. Cl. ........................................ 528/96; 528/97; 528/98; 528/99; 525/396; 549/552
[58] Field of Search .................... 528/96, 97, 98, 99; 525/396; 549/552

[56] References Cited

U.S. PATENT DOCUMENTS

| | | | |
|---|---|---|---|
| 2,712,001 | 6/1955 | Greenlee | 525/523 |
| 3,004,951 | 10/1961 | Dazzi | 528/102 |
| 3,133,033 | 5/1964 | St. Clair et al. | 523/450 |
| 3,291,775 | 12/1966 | Holm | 528/121 |
| 3,374,203 | 3/1968 | Schmukler | 528/87 |
| 3,378,525 | 4/1968 | Sellers | 528/98 |
| 3,386,953 | 6/1968 | Dunning et al. | 525/523 |
| 3,477,990 | 11/1969 | Fogg | 528/89 |
| 3,484,408 | 12/1969 | Holm | 528/111 |
| 3,547,881 | 12/1970 | Mueller et al. | 528/89 |
| 3,774,305 | 11/1973 | Stoffey et al. | 523/116 |
| 3,784,516 | 1/1974 | Baxter et al. | 525/495 |
| 3,907,768 | 9/1975 | van der Veen et al. | 252/408 |
| 3,919,317 | 11/1975 | Huff et al. | 564/276 |
| 4,027,950 | 6/1977 | Moriyama et al. | 252/299 |
| 4,045,408 | 8/1977 | Griffith et al. | 252/182 |
| 4,072,656 | 2/1978 | Hartmann | 427/195 |
| 4,153,621 | 5/1979 | Hartmann | 528/87 |
| 4,349,619 | 9/1982 | Kamoshida et al. | 430/196 |
| 4,480,082 | 10/1984 | McLean et al. | 528/103 |
| 4,499,255 | 2/1985 | Wang et al. | 528/95 |
| 4,594,291 | 6/1986 | Bertram et al. | 428/414 |
| 4,594,373 | 6/1986 | Kohli | 523/400 |
| 4,595,761 | 6/1986 | Chattha | 546/263 |
| 4,609,719 | 9/1986 | Chattha | 528/98 |
| 4,611,046 | 9/1986 | Chattha | 528/98 |
| 4,611,047 | 9/1986 | Chattha | 528/114 |
| 4,636,535 | 1/1987 | Wang et al. | 523/204 |
| 4,645,803 | 2/1987 | Kohli et al. | 525/423 |
| 4,663,401 | 5/1987 | Saito et al. | 525/505 |
| 4,717,674 | 1/1988 | Sung | 534/588 |
| 4,745,135 | 5/1988 | Thomas et al. | 521/114 |
| 4,745,136 | 5/1988 | Thomas et al. | 521/114 |
| 4,745,137 | 5/1988 | Thomas et al. | 521/137 |
| 4,758,636 | 7/1988 | Hijikata et al. | 525/438 |
| 4,762,901 | 8/1988 | Dhein et al. | 528/73 |
| 4,791,154 | 12/1988 | Corley | 523/456 |
| 4,962,163 | 10/1990 | Hefner et al. | 525/463 |
| 5,077,380 | 12/1991 | Hefner et al. | 528/322 |
| 5,182,340 | 1/1993 | Hefner et al. | 525/525 |

FOREIGN PATENT DOCUMENTS

| | | |
|---|---|---|
| 252358A | 1/1988 | European Pat. Off. . |
| 0282963 | 8/1988 | European Pat. Off. . |
| 4217660 | 9/1942 | Japan . |
| 56-152830 | 11/1981 | Japan . |
| 58-206579 | 5/1982 | Japan . |
| 62-96484 | 5/1987 | Japan . |
| 63-10617 | 1/1988 | Japan . |

OTHER PUBLICATIONS

Chattha et al., in *Journal of applied Polymer Science,* 1987, pp. 1829 to 1834.
C. Lin et al., in *Side-Chain Liquid Crystal Epoxy Polymers,* Aug. 1990, pp. 665 to 666.
Chem. Abst. 68(18):79112y, 1968.
Varma and Kothari in *Indian Journal of Technology,* Jul., 1983, pp. 265 to 267.
Eichler and Mleziva in *Die Angewandte Makromolekulare,* 1971, pp. 31 to 55.
Dobas and Eichler in Faserforschung und Textiltechnik, *Zeitschrift fur Polymerforschung,* 1977, pp. 589 to 594.

(List continued on next page.)

*Primary Examiner*—Morton Foelak
*Assistant Examiner*—Rachel Johnson

[57] ABSTRACT

Phenoxy resins are disclosed which are prepared from polyglycidyl amines containing one or more mesogenic moieties. The phenoxy resins are useful in the preparation of coatings.

1 Claim, No Drawings

OTHER PUBLICATIONS

Chem. Abst. 95:97564j, 1981.
Chem. Abst. 95:116389z, 1981.
Derwent 59720a/33, 1976.
Derwent 61196w/37, 1973.
Derwent 90978y/51, 1976.
Derwent 84-004219/01, 1981.
Chem. Abst. 72(4) 13864w, 1970.
Chem. Abst. 70(12):48668w, 1969.
Chem. Abst. 70(6):20598z, 1969.
Chem. Abst. 108(5):37570k, 1988.
Chem. Abst. 103(2):6739q, 1985.
Chem. Abst. 98(20):161437m, 1983.
Chem. Abst. 91(10):75371j, 1979.
Chem. Abst. 90(26):205248s, 1979.
Chem Abst. 90(12):88268k, 1979.
Chem. Abst. 92(14):111622y, 1980.
Chem. Abst. 91(10):75283q, 1971.
Chem. Abst. 100(15):120861m, 1984.
Chem. Abst. 100(24):192949u, 1984.
Chem. Abst. 101(20):172329j, (1984).
Chem. Abst. 111(18):155027y, 1989.
Chem. Abst. 109(4):23706t, 1988.
Chem. Abst. 104(19):168349k, 1986.
Chem. Abst. 102(24):204848s, 1985.
Chem. Abst. 101:192592t, 1984.
Chem. Abst. 104:6259d, 1986.
Chen. Abst. 106:52298e, 1987.
Chem. Abst. 60:5407g, 1960.
Chem. Abst. 90:138566d, 1979.
Chem. Abst. 92:59604c, 1980.
Chem. Abst. 93(22):213243p, 1980.
Chem. Abst. 91(25):211190d, 1979.
Chem. Abst. 91(24):193677m, 1979.
Chem. Abst. 91(24):193675j, 1979.
Chem. Abst. 90(16):122448f, 1979.
Chem. Abst. 90(2):6882u, 1979.
Derwent Abstract 85-173653/29, 1985.

MESOGENIC GLYCIDYL AMINES

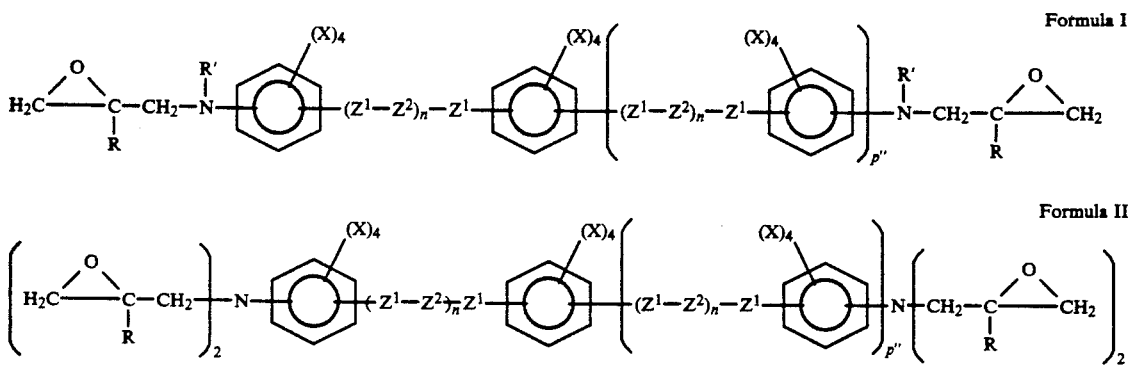

CROSS-REFERENCE TO RELATED APPLICATIONS

This application is a continuation-in-part of application serial number 07/663,499 filed Mar. 1, 1991, now abandoned, which is a continuation-in-part of application Ser. No. 07/562,289 filed Aug. 3, 1990 which are incorporated herein by reference in their entirety.

FIELD OF THE INVENTION

The present invention concerns glycidyl amines of mono and polyamines containing one or more mesogenic moieties, curable compositions and cured compositions thereof.

BACKGROUND OF THE INVENTION

Glycidyl amines are a specialized class of thermosettable resins with utility in a myriad of applications, notably coatings, adhesives, encapsulants, moldings, laminates, castings, electrical insulation, weatherable coatings, sealants, impregnants, plasticizers, fibers, foams, and the like. The art, describes numerous incremental improvements in the physical, mechanical, thermal and/or chemical resistant properties possessed by certain polyglycidyl amines relative to their polyglycidyl ether counterparts. This nonwithstanding, substantial room for improvement in one or more of the aforesaid properties of polyglycidyl amines is desireable for each of the aforementioned applications.

The present invention provides a method for improving the properties of mono and polyglycidyl amines as well as the curable and cured compositions thereof by incorporating one or more mesogenic moieties into the structure of said glycidyl amines. These glycidyl, amines exhibit ordering of the molecular chains in the melt phase and/or in the advanced compositions thereof. This morphology is susceptible to orientation during processing which can result in enhanced unidirectional mechanical properties. This is not possible to any significant extent with the conventional (non-mesogenic) glycidyl amines. The mesogenic structures incorporated into the structure of the glycidyl amines and the polymer chains of the resultant polymers thereof are believed to be responsible for the improvement in properties.

SUMMARY OF THE INVENTION

One aspect of the present invention pertains to polyglycidyl amines containing one or more mesogenic moieties represented by the following Formulas I and II wherein at least about 80 percent of the $-(Z^1-Z^2)n-Z^1-$ linkages and the glycidyl amine groups are in the para position with respect to each other: each R and $R^1$ is independently hydrogen or an aliphatic hydrocarbon group having from 1 to about 4 carbon atoms; each R' is independently a hydrocarbyl group having suitably from 1 to about 12, more suitably from I to about 6, most suitably from 1 to about 2, carbon atoms; each X is independently hydrogen, a hydrocarbyl or hydrocarbyloxy group having suitably from 1 to about 12, more suitably from 1 to about 6, most suitably from 1 to about 4. carbon atoms, a halogen atom (preferably chlorine or bromine), $-NO_2$, or $-C\equiv N$; each $Z^1$ is independently a direct single bond, $-CR^1=CR^1-$, $-CR^1=C-R^1-CR^1=CR^1-$, $-CR^1=N-N=CR^1-$, $-CR^1=CR^1-CO-O-(CHR^1)_{p'}-$, $-CR^1=C-R^1-O-CO-(CHR^1)P,-$, $-(CHR^1)p$, $-O-CO-CR^1=CR^1-$, $-(CHR^1)_{p'}-CO-O-CR^1=C-R^1-$, $-CR^1=CR^1-CO-O-$, $-O-CO-CR^1=C-R^1-$, $-CO-NR^1-$, $-NR^1-CO-$, $-CO-NR^1-NR-CO-$, $-C\equiv C-$, $-C\equiv C-C\equiv C-$, $-CO-S-$, $-S-CO-$, $-CR^1=N-$, $-N=CR^1-$, $-O-CO-$, $-CO-O-$, $-CR^1=CR^1-CO-$, $-CO-CR^1=CR^1-$, $-CR^1=CR^1-O-CO-$, $-CO-O-CR^1=CR-$, $-CH_2-CH_2-CO-O-$, $-O-CO-CH_2-CH_2-$, $-N=N-$,

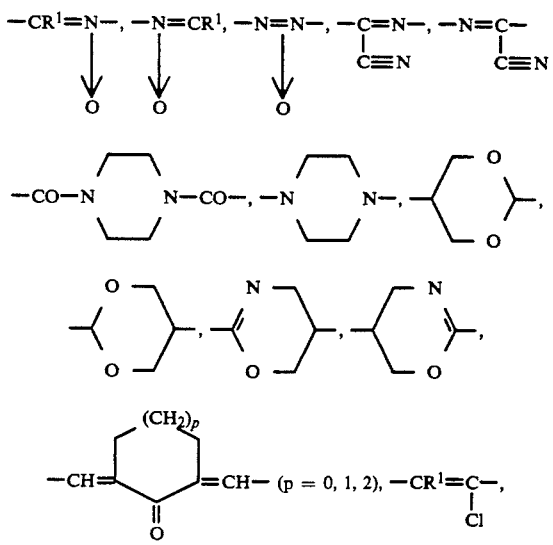

-continued

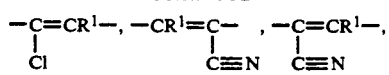

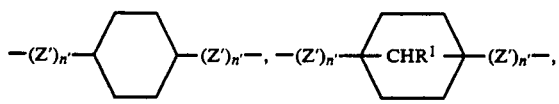

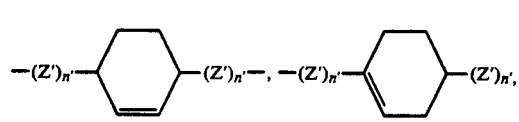

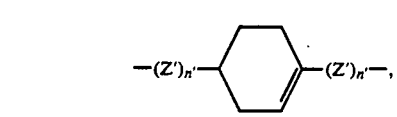

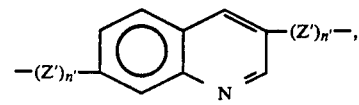

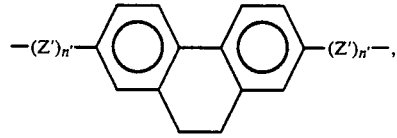

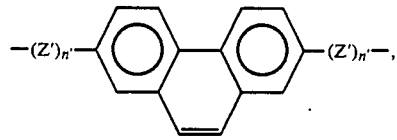

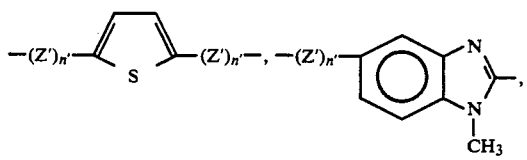

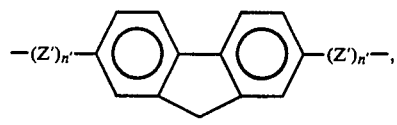

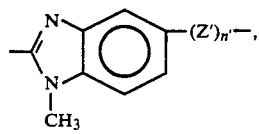

-continued

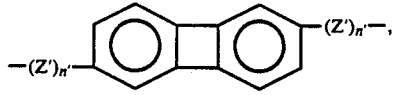

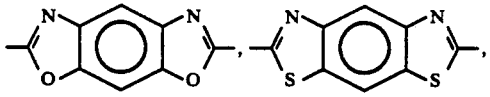

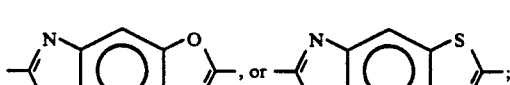

$Z^2$ is a group represented by a cyclic or bicyclic ring system containing from 5 to about 12 carbon atoms and may be cycloaliphatic, polycycloaliphatic, aromatic or a combination thereof; n is zero to 1; p' is 1 or 2; p'' has a value of zero to 100; each Z' is independently a —CO—, —O—CO—, —CO—O—, —CO—NR$^1$—, or —NR$^1$—CO— group and each n' independently has a value of zero or one; with the proviso that the polyglycidyl amine of Formula II is not the tetraglycidyl amine of 4,4'-diaminobiphenyl (R is H, X is H, n=O, p''=O, $Z^1$ is a direct single bond) or the tetraglycidyl amine of 3,3'-dimethyl-4,4'-diaminobiphenyl (R is H, X in the 3,3'-dimethyl-4,4'-diaminobiphenyl (R is H, X in the 3,3' position is —CH$_3$ and H in all other positions, n=O, p''=O, $Z^1$ is a direct single bond).

Another aspect of the present invention pertains to polyglycidyl amines containing one or more mesogenic moieties represented by the following Formulas III and IV Formula III

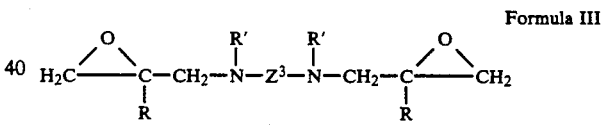

Formula IV

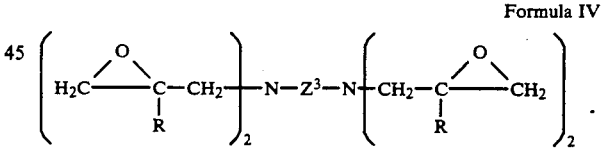

wherein $Z^3$ is

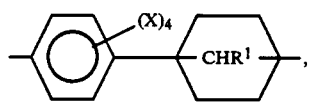

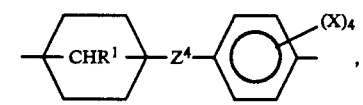

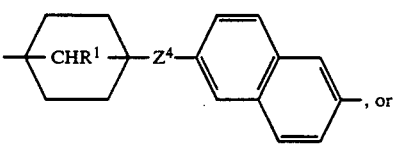

, or

-continued

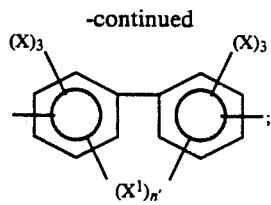

and $Z^4$ is —CO—O—, —O—CO—, —NR$^1$—CO— or —CO—NR$^1$—; $X^1$ is a divalent hydrocarbyl group having from 1 to about 10, preferably from 1 to about 4, carbon atoms which can contain one or more heteroatoms selected from N, O, S and the like and may be saturated or unsaturated; each R and $R^1$ is independently hydrogen or an aliphatic hydrocarbon group having from 1 to about 4 carbon atoms; each R' is independently a hydrocarbyl group having suitably from 1 to about 12, more suitably from 1 to about 6, most suitably from 1 to about 2, carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; and n' is zero or one.

Another aspect of the present invention pertains to diglycidyl amine compounds containing one or more mesogenic moieties represented by the following Formula V

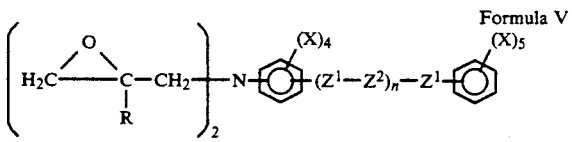

Formula V wherein at least about 80 percent of the —($Z^1$—$Z^2$)$_n$—$Z^1$— linkages and the glycidyl amine groups are in the para position with respect to each other; R, $R^1$, X, $Z^1$, $Z^2$, Z', n, p' and n' are as hereinbefore defined.

Another aspect of the present invention pertains to diglycidyl amine compounds containing one or more mesogenic moieties represented by the Formula VI

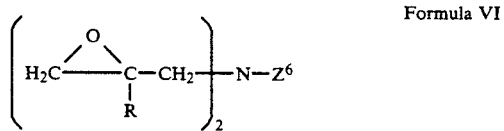

Formula VI wherein R, $R^1$, X, $X^1$, $Z^4$ and n' are as hereinbefore defined; and $Z^6$ is

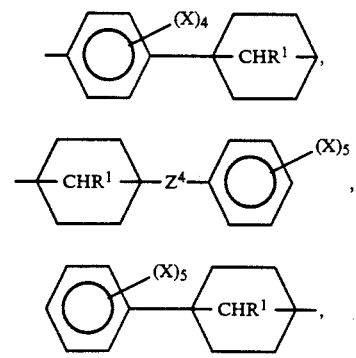

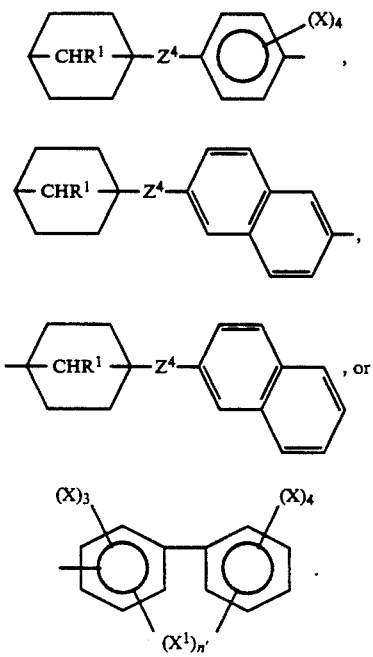

Another aspect of the present invention pertains to monoglycidyl amine compounds containing one or more mesogenic moieties represented by the following Formula VII

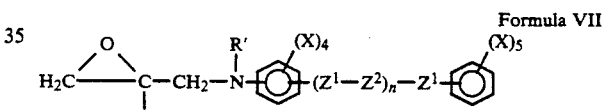

Formula VII wherein at least about 80 percent of the —($Z^1$—$Z^2$)$_n$—$Z^1$— linkages and the glycidyl amine groups are in the para position with respect to each other; R, R', $R^1$, X, $Z^1$, $Z^2$, Z', n, p' and n' are as hereinbefore defined.

Another aspect of the present invention pertains to monoglycidyl amine compounds containing one or more mesogenic moieties represented by the following Formula VIII

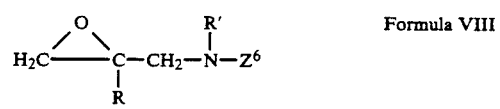

Formula VIII wherein R, R', $R^1$, X, $X^1$, $Z^3$, $Z^4$ and n' are as hereinbefore defined and $Z^6$ is

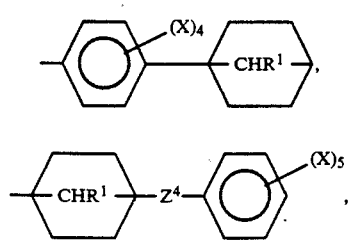

-continued

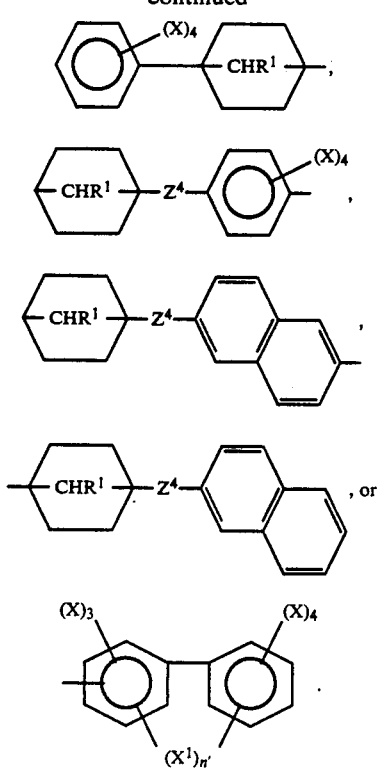

Another aspect of the present invention pertains to advanced polyglycidyl amine compositions prepared by reacting (A) one or more of the polyglycidyl amines containing one or more mesogenic moieties, said polyglycidyl amines being those represented by Formulas I–VI, with the proviso that the polyglycidyl amine of Formula II may include the tetraglycidyl amine of 4,4'-diaminobiphenyl or the tetraglycidyl amine of 3,3'-dimethyl-4,4'-diaminobiphenyl; with (B) at least one compound having an average of more than one active hydrogen atom per molecule; and wherein components (A) and (B) are employed in quantities which provide a ratio of active hydrogen atoms per epoxide group of from about 0.01:1 to about 0.95:1, more suitably from about 0.05:1 to about 0.8:1, most suitably from about 0.1:1 to about 0.5:1;

with the proviso that when component (A) contains polyglycidyl amine compounds containing an average of more than two glycidyl groups per molecule, such compounds are present in an amount such that less than about 15, preferably less than about 10, more preferably less than about 5 percent of the glycidyl groups are contributed by the compounds containing an average of more than two glycidyl groups per molecule.

Another aspect of the present invention pertains to phenoxy type resin compositions prepared by the advancement reaction of (A) one or more of the polyglycidyl amines containing one or more mesogenic moieties, said polyglycidyl amines being those represented by either Formulas I, III, V or VI; with (B) at least one compound having an average of more than one active hydrogen atom per molecule; and wherein components (A) and (B) are employed in quantities which provide a ratio of active hydrogen atoms per epoxide group of from about 0.96:1 to about 1.05:1.

Another aspect of the present invention pertains to blends of (A) one or more of the polyglycidyl amines or monoglycidyl amine compounds containing one or more mesogenic moieties which polyglycidyl amines or monoglycidyl amine compounds are represented by the aforementioned Formulas I–VIII with the proviso that the polyglycidyl amine of Formula II may include the tetraglycidyl amine of 4,4'-diaminobiphenyl or the tetraglycidyl amine of 3,3'-dimethyl-4,4'-biphenyl; and (B) one or more polyepoxides represented by the following Formulas IX–XV;

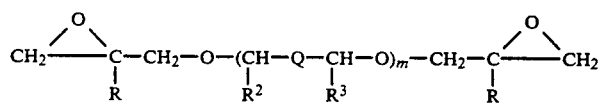

Formula IX

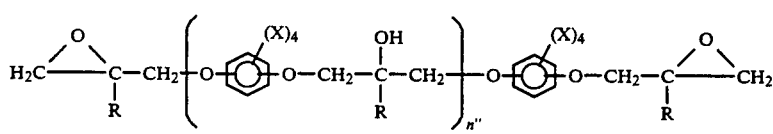

Formula X

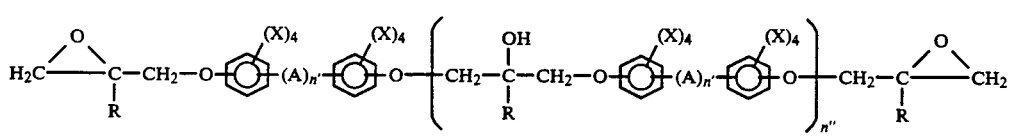

Formula XI

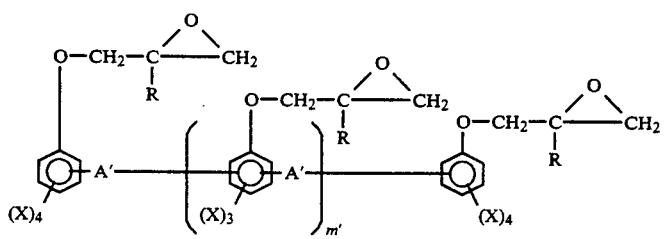

Formula XII

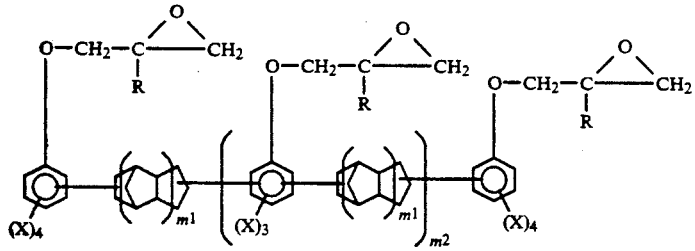

Formula XIII

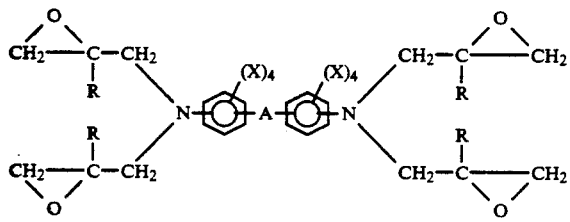

Formula XIV

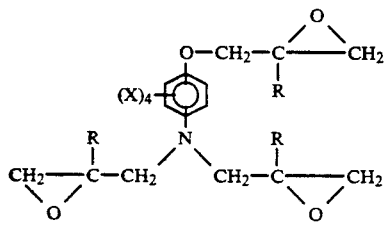

Formula XV wherein each A is independently a divalent hydrocarbyl group having from 1 to about 12, preferably from about 1 to about 6, more preferably from 1 to about 3, carbon atoms, —O—, —S—, —S—S—, —SO—, —SO$_2$—, or —CO—; each A' is independently a divalent hydrocarbon group having from 1 to about 6, preferably from 1 to about 3, carbon atoms; Q is a single bond, —CH$_2$—S—CH$_2$—, —(CH$_2$)$_{n'}$—, or

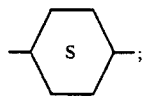

each R is independently hydrogen or an alkyl group having from 1 to about 4 carbon atoms; each $R^2$ and $R^3$ is independently hydrogen, a hydrocarbyl or halohydrocarbyl group having from 1 to about 6, preferably from 1 to about 3, more preferably from 1 to about 2, carbon atoms; each X is independently hydrogen, a hydrocarbyl or hydrocarbyloxy group having from 1 to about 12, preferably from about 1 to about 6, most preferably from 1 to about 4, carbon atoms, a halogen atom, —NO$_2$ or —C≡N; m has a value from about 1 to about 10, preferably from about 1 to about 4, more preferably from about 1 to about 2; m' has an average value from about 0.01 to about 12, preferably from about 1 to about 6, more preferably from about 1 to about 3; $m^1$ has an average value from about 1 to about 12, preferably from about 1 to about 6, more preferably from about 1 to about 3; $m^2$ has a value from about 1 to about 12, preferably from about 2 to about 6, more preferably from about 2 to about 3; n' has a value of zero or 1; n'' has an average value from about zero to about 3, preferably from about zero to about 1.5, more preferably from about zero to about 0.5, and $n^1$ has an average value from about 1 to about 10; and wherein component (A) is present in an amount suitably from about 1 to about 99, more suitably from about 10 to about 80, most suitably from about 10 to about 50, percent by weight based upon the combined weight of components (A) and (B) and component (B) is present in an amount suitably from about 99 to about 1, more suitably from about 90 to about 20, most suitably from about 90 to about 50, percent by weight based upon the combined weight of components (A) and (B).

Another aspect of the present invention pertains to blends of (A) one or more of the advanced polyglycidyl amines containing one or more mesogenic moieties which advanced polyglycidyl amines are prepared by reacting (1) one or more polyglycidyl amines represented by Formulas I–VI, with the proviso that the polyglycidyl amine of Formula II may include the tetraglycidyl amine of 4,4'-diaminobiphenyl or the tetraglycidyl amine of 3,3'-dimethyl-4,4'-diaminobiphenyl, and (2) at least one compound having an average of more than one active hydrogen atom per molecule; and (B) one or more polyepoxides represented by Formulas IX–V; and wherein component (A) is present in an amount suitably from about 1 to about 99, more suitably from about 10 to about 80, most suitably from about 10 to about 50, percent by weight based upon the combined weight of components (A) and (B) and component (B) is present in an amount suitably from about 99 to about 1, more suitably from about 90 to about 20, most suitably from about 90 to about 50, percent by weight based upon the combined weight of components (A) and (B).

Another aspect of the present invention pertains to curable compositions comprising at least one polyglycidyl amine containing one or more mesogenic moieties represented by Formulas I–VI and a curing amount of a suitable curing agent therefor.

Another aspect of the present invention pertains to curable compositions comprising (A) at least one polyglycidyl amine containing one or more mesogenic moieties, said polyglycidyl amine being represented by either Formulas I–VI, with the proviso that the polyglycidyl amine of Formula II may include the tetraglycidyl amine of 4,4'-diaminobiphenyl or the tetraglycidyl amine of 3,3'-dimethyl-4,4'-diaminobiphenyl;

(B) at least one of the aforementioned monoglycidyl amine compounds containing one or more mesogenic moieties, said monoglycidyl amine compounds being represented by Formulas VII or VIII, and (C) a curing amount of a suitable curing agent therefor; wherein component (A) is present in an amount suitably from about 1 to about 99, more suitably from about 50 to about 90, most suitably from about 70 to about 90, percent by weight based upon the combined weight of components (A) and (B) and component (B) is present in an amount suitably from about 99 to about 1, more suitably from about 50 to about 10, most suitably from about 30 to about 10, percent by weight based upon the combined weight of components (A) and (B).

Another aspect of the present invention pertains to curable compositions comprising (A) one or more of the advanced polyglycidyl amines resulting from reacting (1) at least one of the polyglycidyl amines containing one or more mesogenic moieties, said polyglycidyl amines being those represented by Formulas I–VI, with the proviso that the polyglycidyl amine of Formula II may include the tetraglycidyl amine of 4,4'-diaminobiphenol or the tetraglycidyl amine of 3,3'-dimethyl-4,4'-diaminobiphenyl; with (2) at least one compound having an average of more than one active hydrogen atom per molecule; wherein components (A1) and (A2) are employed in quantities which provide a ratio of active hydrogen atoms to epoxide groups suitably from about 0.01:1 to about 0.95:1, more suitably from about 0.05:1 to about 0.8:1, most suitably from about 0.1:1 to about 0.5:1; and (B) a curing amount of a suitable curing agent for component (A).

Another aspect of the present invention pertains to curable compositions comprising a blend of (A) at least one of the polyglycidyl amines or monoglycidyl amine compounds containing one or more mesogenic moieties represented by Formulas I–VIII, with the proviso that the polyglycidyl amine of Formula II may include the tetraglycidyl amine of 4,4'-diaminobiphenyl or the tetraglycidyl amine of 3,3'-dimethyl-4,4'-diaminobiphenyl;

(B) at least one of the polyepoxides resins represented by Formulas IX–XV; and (C) a curing amount of a suitable curing agent therefor; wherein component (A) is present in an amount suitably from about 1 to about 99, more suitably from about 10 to about 80, most suitably from about 10 to about 50, percent by weight based upon the combined weight of components (A) and (B) and component (B) is present in an amount suitably from about 99 to about 1, more suitably from about 90 to about 20, most suitably from about 90 to about 50, percent by weight based upon the combined weight of components (A) and (B).

Another aspect of the present invention pertains to curable compositions comprising a blend of (A) at least one of the advanced polyglycidyl amines containing one or more mesogenic moieties prepared by reacting (1) one or more polyglycidyl amines represented by Formulas I–VI, with the proviso that the polyglycidyl amine of Formula II may include the tetraglycidyl amine of 4,4'-diaminobiphenyl or the tetraglycidyl amine of 3,3'-dimethyl-4,4'-diaminobiphenyl; with (2) at least one compound having an average of more than one active hydrogen atom per molecule; wherein components (1) and (2) are employed in quantities which provide a ratio of active hydrogen atoms per epoxide group suitably from about 0.01:1 to about 0.95:1, more suitably from about 0.05:1 to about 0.8:1, most suitably from 0.1:1 to about 0.5:1;

(B) at least one of the polyepoxide resins represented by Formulas IX–XV; and (C) a curing amount of a suitable curing agent therefor; wherein component (A) is present in an amount suitably from about 1 to about 99, more suitably from about 10 to about 80, most suitably from about 10 to about 50, percent by weight based upon the combined weight of components (A) and (B) and component (B) is present in an amount suitably from about 99 to about 1, more suitably from about 90 to about 20, most suitably from about 90 to about 50, percent by weight based upon the combined weight of components (A) and (B).

A further aspect of the present invention pertains to products resulting from curing the aforementioned curable compositions.

A further aspect of the present invention pertains to products resulting from the application of an electric field or magnetic field or drawing and/or shear forces before and/or during curing or processing of the aforementioned compositions.

A still further aspect of the present invention pertains to products resulting from the application of an electric field or magnetic field or drawing and/or shear forces before and/or during curing or processing of a curable composition comprising (A) at least one polyglycidyl amine containing one or more mesogenic moieties said polyglycidyl amines being those represented by Formulas I–VI, with the proviso that the polyglycidyl amine of Formula II may include the tetraglycidyl amine of 4,4'-diaminobiphenyl or the tetralycidyl amine of 3,3'-dimethyl-4,4'-diaminobiphenyl; and (B) a curing amount of at least one suitable curing agent for component (A).

The term "mesogenic" as is used herein designates compounds containing one or more rigid rodlike structural units which have been found to favor the formation of liquid crystal phases in the case of low molar mass substances. Thus the mesogen or mesogenic moiety is that structure responsible for molecular ordering.

DETAILED DESCRIPTION OF THE INVENTION

The mono and polyglycidyl amine compositions of the present invention can be prepared by any suitable method known to those skilled in the art. One such suitable method includes reaction of a mono or diamine and an epihalohydrin to form the corresponding halohydrin amine of said mono or diamine followed by dehydrohalogenation of the resultant halohydrin amine. In the preparation of the mono or polyglycidyl amine of a mono or polyamine, the amine containing compound is typically reacted with an epihalohydrin in the presence or absence of a suitable catalyst and in the presence or absence of a suitable solvent at a temperature suitably from about 0° C. to about 150° C., more suitably from about 20° C. to about 100° C., most suitably from about 40° C. to about 80° C.; at pressures suitably from about 30 mm Hg vacuum to about 100 psia., more suitably from about 65 mm Hg vacuum to about 50 psia., most suitably from about atmospheric pressure to about 20 psia.; and for a time sufficient to complete the reaction, usually from about 1 to about 48, more usually from about 1 to about 12, most usually from about 1 to about 6 hours. This initial reaction unless the catalyst is an alkali metal or alkaline earth metal hydroxide employed in stoichiometric quantities produces a halohydrin amine intermediate which is then reacted with a basic acting compound to convert the vicinal halohydrin groups to epoxide groups. Reaction of the halohydrin amine intermediate and basic acting compounds in the presence or absence of a suitable solvent is typically conducted at a temperature suitably from about 0° C. to about 100° C., more suitably from about 20° C. to 80° C., most suitably from about 2° C. to about 60° C.; at pressures suitably from about 30 mm Hg vacuum to about 100 psia., more suitably from about 45 mm Hg vacuum to about 50 psia., most suitably from about 60 mm Hg vacuum to atmospheric pressure; and for a time sufficient to complete the dehydrohalogenation reaction, usually from about 10 minutes to about 12 hours, more usually from about 15 minutes to about 6 hours, most usually from about 20 minutes to about 1 hour. The resultant product is a glycidyl amine compound.

Suitable epihalohydrins which can be employed to prepare the mono and polyglycidyl amines of the present invention include, for example, those represented by the following Formula XVI

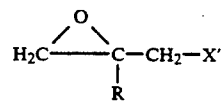

Formula XVI wherein R is as previously defined and X' is a halogen. Particularly suitable such epihalohydrins include, for example, epichlorohydrin, epibromohydrin, epiiodohydrin, methylepichlorohydrin, methylepibromohydrin, methylepiiodohydrin, combinations thereof and the like.

Suitable amine containing compounds which can be employed to prepare the mono and polyglycidyl amines of the present invention include, for example, those represented by the following Formulas XVII–XXIV

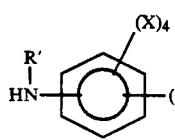

Formula XVII

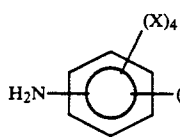

Formula XVIII

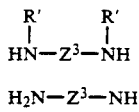

Formula XIX

Formula XX

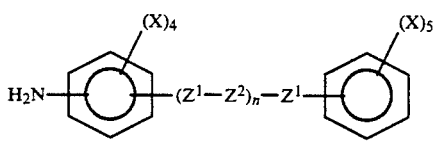

Formula XXI

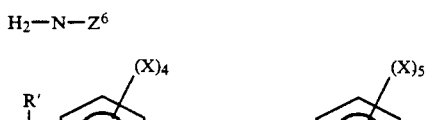

Formula XXII

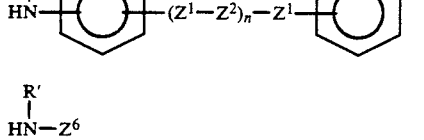

Formula XXIII

Formula XXIV wherein at least about 80 percent of the $-(Z^1-Z^2)_n-Z^1-$ linkages and the amine groups are in the para position with respect to each other; wherein R', R$^1$, X, X$^1$, Z$^1$, Z$^2$, Z$^3$, Z$^4$, Z$^6$, n, n', and p'' are as previously defined.

Particularly suitable amine containing compounds include, for example, 4,4'-diamino-α-methylstilbene, 4,4'-diaminobenzanilide, 4,4'-diamino-2,2'-dimethylazoxybenzene, 4,4'-diaminostilbene, 4,4'-diaminoazobenzene, 4,4'-diaminoazoxybenzene, 4,4'-diamino-α-cyanostilbene, 4,4'-diaminodiphenylacetylene, N,N'-bis(4-aminophenyl)terephthalamide, 4,4'-diamino-3,3',5,5'-tetramethylstilbene, 4,4'-diamino-3,3',5,5'-tetrabromostilbene, 4,4'-diamino-3,3',5,5'-tetramethyl-α-methylstilbene, N-biphenyl-4-aminobenzamide, N-2-naphthyl-4-aminobenzamide, N-phenyl-4-aminobenzamide, N-(4'-aminophenyl)benzamide, 4-aminostilbene, 4-amino-α-methylstilbene, 4-aminoazobenzene, 4-amino-α-cyanostilbene, 4-aminoazoxybenzene, 4,4'-diaminodiphenylazomethine, 4-amino-4l-methoxystilbene, N,N'-dimethyl-4,4'-diaminobiphenyl, N,N'-dimethyl-3,3'-dimethyl-4,4'-diaminobiphenyl, N,N'-dimethyl-4,4'-diamino-α-methylstilbene, N,N'-diethyl-4,4'-diamino-α-methylstilbene, N,N'-dimethyl-4,4'-diaminobenzanilide, N,N'-dimethyl-4,4'-diaminostilbene, N,N'-dimethyl-4,4'-diaminoazoxybenzene, N,N'-dimethyl-4,4'-diamino-α-cyanostilbene, N,N'-dimethyl-4,4'-diamino-α-chlorostilbene, N,N'-dimethyl-4,4'-diaminodiphenylacetylene, N,N'-dimethyl-4,4'-diamino-3,3',5,5'-tetramethylstilbene, N,N'-diethyl-4,4'-diamino-α,α'-dimethylstilbene, N-methyl-4-aminostilbene, N-ethyl-4-aminostilbene, N-methyl-4-amino-α-methylstilbene, N-methyl-4-aminoazobenzene, N-methyl-4-amino-α-cyanostilbene, N-methyl-4-aminoazoxybenzene, N-methyl-4-aminobenzamide, N-methyl-4-amino-4'-methoxystilbene, N,N'-dimethyl-4-aminobenzamide, N-methyl-4-amino-α-chlorostilbene, N,N'-dimethyl-4,4'-diaminodiphenylazomethine, combinations thereof and the like.

Suitable catalysts which can be employed to prepare the mono and polyglycidyl amines of the present invention include, for example, ammonium halides such as, for example, benzyltrimethylammonium chloride, benzyltrimethylammonium bromide, tetrabutylammonium chloride, tetrabutylammonium bromide, tetraoctylammonium chloride, tetraoctylammonium bromide, tetramethylammonium chloride, tetramethylammonium bromide, combinations thereof and the like.

Suitable basic acting compounds which can be employed to prepare the mono and polyglycidyl amines of the present invention include, for example, alkali metal or alkaline earth metal hydroxides, carbonates, bicarbonates and the like. Particularly suitable such compounds include, for example, sodium hydroxide, potassium hydroxide, lithium hydroxide, calcium hydroxide, barium hydroxide, magnesium hydroxide, manganese hydroxide, sodium carbonate, potassium carbonate, lithium carbonate, calcium carbonate, barium carbonate, magnesium carbonate, manganese carbonate, sodium bicarbonate, potassium bicarbonate, lithium bicarbonate, calcium bicarbonate, barium bicarbonate, magnesium bicarbonate, manganese bicarbonate, mixtures thereof and the like. Most preferred is sodium hydroxide or potassium hydroxide.

Suitable solvents which can be employed herein include, for example, alcohols, glycols, aliphatic hydrocarbons, aromatic hydrocarbons, glycol ethers, amides, sulfoxides, sulfones, combinations thereof and the like. Particularly suitable solvents include, for example, methanol, ethanol, isopropanol, hexane, heptane, octane, nonane, decane, toluene, xylene, ethylene glycol, propylene glycol, ethylene glycol methyl ether, ethylene glycol ethyl ether, ethylene glycol n-butyl ether, ethylene glycol phenyl ether, propylene glycol methyl ether, propylene glycol phenyl ether, tripropylene glycol methyl ether, diethylene glycol methyl ether, diethylene glycol ethyl ether, diethylene glycol n-butyl ether, diethylene glycol phenyl ether, butylene glycol meluhyl ether, N,N-dimethylformamide, N-methylpyrrolidinone, N,N-dimethylacetamide, dimethylsulfoxide, sulfolane, combinations thereof and the like.

The solvent, if used, is usually employed in amounts suitably from about 5 to about 95, more suitably from about 20 to about 60, most suitably from about 30 to about 40, percent by weight based upon the combined weight of solvent and epihalohydrin.

Suitable compounds having an average of more than one active hydrogen atom per molecule which can be employed to prepare the advanced resin compositions of the present invention include, for example, bisphenols, thiobisphenols, dicarboxylic acids and compounds containing one primary amine or amide group or two secondary amine groups such as those represented by the following Formulas XXV or XXVI;

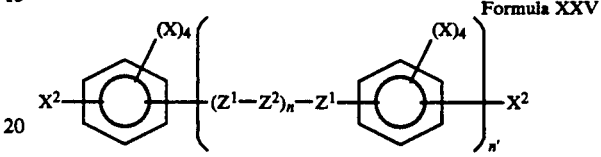

Formula XXV

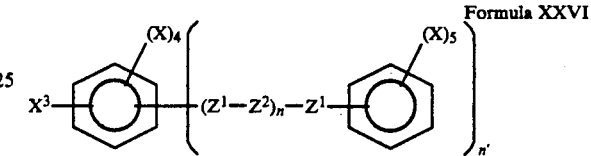

Formula XXVI wherein $X^2$ is independently a hydroxyl, carboxylic acid, —SH, or —NHR' group; $X^3$ is —NH$_2$, NH$_2$—SO$_2$—, NH$_2$—CO—, or NH$_2$—Z$^5$—O—; $Z^5$ is an alkyl or cycloalkyl group having from 1 to about 12 carbon atoms; and wherein R', Z', X, Z', R$^1$, Z$^2$, n and n' are as hereinbefore defined.

The advancement of the polyglycidyl amines containing one or more mesogenic moieties with compounds having an average of more than one active hydrogen per molecule is employed to linearly chain extend the resin. This linear chain extension is required for some mesogen-containing resin compositions in order to obtain liquid crystal character. The advancement of the mesogenic polyglycidyl amine resins can also be used to increase the temperature range in which a particular resin is liquid crystalline and to control the degree of crosslinking during the final curing stage.

The polyglycidyl amine containing one or more mesogenic moieties and the compound having an average of more than one active hydrogen atom per molecule are reacted in amounts which provide suitably from about 0.01:1 to about 0.95:1, more suitably from about 0.05:1 to about 0.9:1, ,most suitably from about 0.10:1 to about 0.50:1 active hydrogen atoms per epoxy group.

Particularly suitable compounds having an average of more than one active hydrogen atom per molecule which can be employed herein include hydroxyl-containing compounds, carboxylic acid-containing compounds and primary amine-containing compounds. These compounds include, for example, those represented by Formulas XXV and XXVI.

Particularly suitable hydroxyl-containing compounds include, for example, hydroquinone, bisphenol A, 4,4'-dihydroxydiphenylmethane, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3',5,5'-tetrachorobisphenol A, 3,3'-dimethoxybisphenol A, 4,4'-dihydroxybiphenyl, 4,4'-dihydroxy-α,α'-diethylstilbene, 4,4'-dihydroxy-α-methylstilbene, 4,4'-dihydroxybenzanilide, 4,4'-dihydroxy-2,2'-dimethylazoxybenzene, 4,4'-dihydroxy-α-cyanostilbene, bis(4-hydroxyphenyl)terephthalate, N,N'-bis(4-hydroxyphenyl)terephthalamide, bis(4'-hydroxybiphenyl)terephthalate, 4,4'-dihydroxyphenylbenzoate, bis(4'-hydroxyphenyl)-1,4-benzenediimine, 4,4''-dihydroxybiphenylbenzoate, 1,4-bis(4'-hydroxyphenyl-1'-carboxamide)benzene, 1,4-bis(4'-hydroxyphenyl-1'-carboxy)benzene, 4,4'-bis(4''-hydroxyphenyl-1'''-carboxy)-biphenyl, mixtures thereof and the like.

Particularly suitable carboxylic acid-containing compounds include, for example, terephthalic acid, 4,4'-benzanilide dicarboxylic acid, 4,4'-phenylbenzoate dicarboxylic acid, 4,4'-stilbenedicarboxylic acid, 4,4'-dicarboxybiphenyl, 4,4'-dicarboxydiphenylazomethine, and mixtures thereof and the like.

Particularly suitable primary amine-containing compounds include, for example, aniline, 4'-sulfonamido-N-phenyl benzamide, 4'-sulfonamido-N'-phenyl-4-chlorobenzamide, 4-amino-1-phenylbenzoate, 4-amino-N-phenylbenzamide, N-phenyl-4-aminophenyl-1-carboxamide, phenyl-4-aminobenzoate, biphenyl-4-aminobenzoate, 1-phenyl-4'-aminophenylterephthalate, mixtures thereof and the like.

Particularly suitable bis(secondary amine)-containing compounds include, for example, N,N'-dimethyl-4,4'-diaminodiphenylmethane, N,N'-diethyl-4,4'-diaminodiphenylmethane, N,N'-dimethyl-4,4'-diaminobiphenyl, N,N'-dimethyl-3,31-dimethyl-4,4'-diaminobiphenyl, N,N'-dimethyl-4,4'-diaminostilbene, N,N'-dimethyl-4,4'-diaminodiphenylsulfone, N,N'-dimethyl-4,4'-diaminobenzanilide, N,N'-dimethyl-4,4'-diamino-N-methylbenzanilide, and mixtures thereof and the like.

The advancement reaction can be conducted in the presence of a suitable advancement catalyst such as, for example, phosphines, quaternary ammonium compounds, phosphonium compounds, tertiary amines and the like. Particularly suitable catalysts include, for example, ethyltriphenylphosphonium chloride, ethyltriphenylphosphonium bromide, ethyltriphenylphosphonium iodide, ethyltriphenylphosphonium diacetate (ethyltriphenylphosphonium acetate-acetic acid complex), ethyltriphenylphosphonium phosphate, tetrabutylohosphonium chloride, tetrabutylphosphonium bromide, tetrabutylphosphonium iodide, tetrabutylphosphonium diacetate (tetrabutylphosphonium acetate-acetic acid complex), butyltriphenylphosphonium tetrabromobisphenate, butyltriphenylphosphonium bisphenate, butyltriphenylphosphonium bicarbonate, benzyltrimethylammonium chloride. tetramethylammonium hydroxide, triethylamine, tripropylamine, tributylamine, 2-methylimidazole, benzyldimethylamine, mixtures thereof and the like. Many of these catalysts are described in U.S. Pat. Nos. 3,306,872; 3,341,580; 3,379,684; 3,477,990; 3,547,881; 3,637,590; 3,843,605; 3,948,855; 3,956,237; 4,048,141; 4,093,650; 4,131,633; 4,132,706; 4,171,420; 4,177,216 and 4,366,295, all of which are incorporated herein by reference.

The amount of advancement catalyst depends, of course, upon the particular reactants and catalyst employed; however, it is usually employed in quantities of from about 0.03 to about 3, preferably from about 0.03 to about 1.5, most preferably from about 0.05 to about 1.5 percent by weight based upon the weight of the epoxy-containing compound.

The advancement reaction can be conducted at atmospheric, superatmospheric or subatmospheric pressures at temperatures of f rom about 20° C. to about 260° C. , preferably from about 80° C. to about 240° C. , more preferably from about 100° C. to about 200° C. The time required to complete the advancement reaction depends upon the temperature employed. Higher temperatures require shorter periods of time whereas lower temperatures require longer periods of time. Generally, however, times of from about 5 minutes to about 24 hours, preferably from about 30 minutes to about 8 hours, more preferably from about 30 minutes to about 3 hours are suitable.

If desired, the advancement reaction can be conducted in the presence of one or more solvents. Suitable such solvents include, for example, glycol ethers, aliphatic and aromatic hydrocarbons, aliphatic ethers, cyclic ethers, ketones, amines, amides, combinations thereof and the like. Particularly suitable solvents include, for example, toluene, benzene, xylene, methyl ethyl ketone, methyl isobutyl ketone, diethylene glycol methyl ether, dipropylene glycol methyl ether, dimethylformamide, dimethylsulfoxide, N-methylpyrrolidinone, tetrahydrofuran, propylene glycol methyl ether, combinations thereof and the like. The solvents can be employed in amounts of from about zero to about 80%, preferably from about 20% to about 60%, more preferably from about 30% to about 50% by weight based upon the weight of the reaction mixture.

When the polyglycidyl amine containing one or more mesogenic moieties and the compound having an average of more than one active hydrogen atom per molecule are reacted in amounts which provide from about 0.96:1 to about 1.05:1 active hydrogen atoms per epoxy group, a relatively high molecular weight substantially thermoplastic resinous product is produced. These thermoplastic resin compositions contain little, if any, curable residual epoxide functionality and may even contain an active hydrogen functionality, depending upon which component is employed in excess, the polyglycidyl amine or the active hydrogen containing compound. These phenoxy type resins may thus be processed using the typical processing methods employed with conventional thermoplastic resins, such as, for example, injection molding or extrusion. Thermosetting may, however, be induced, for example, via reaction of all or a part of the backbone secondary aliphatic hydroxyl groups produced in the aforesaid advancement reaction, with a curing agent therefor. One class of suitable curing agents includes, for example, the di or polyisocyanates, as well as the blocked di or polyisocyanates which can be induced to react with the secondary hydroxyl groups providing urethane crosslinks between the resin chains. An example of a specific diisocyanate especially useful herein is 4,4'-diisocyanatodiphenylmethane. If desired, the reaction can be conducted in the presence of a suitable catalyst such as, for example, those catalysts described herein for use in the advancement reaction.

The compositions of the present invention containing an average of more than one vicinal epoxy group per molecule can be cured with any suitable curing agent for curing epoxy-containing resins such as, for example, primary and secondary polyamines, carboxylic acids and anhydrides thereof, aromatic hydroxyl containing compounds, imidazoles, guanidines, urea-aldehyde resins, melamine-aldehydes resins, alkoxylated urea-aldehyde resins, alkoxylated melamine-aldehyde resins, aliphatic amines, cycloaliphatic amines, aromatic amines, combinations thereof and the like. Said curing agents may contain one or more mesogenic moieties or may be substantially free of said mesogenic moieties. Particularly suitable curing agents include, for example, diaminodiphenylmethanes, dicyandiamide, ethylene diamine, diethylenetriamine, triethylenetetramine, tetraethylenepentamine, urea-formaldehyde resins, melamine-formaldehyde resins, methylolated urea-formaldehyde resins, methylolated melamine-formaldehyde resins, phenol-formaldehyde novolac resins, cresol-formaldehyde novolac resins, sulfanilamide, diaminodiphenylsulfones, diethyltoluenediamines, t-butyltoluenediamines, bis-4-aminocyclohexylmethane, isophoronediamine, diaminocyclohexanes, hexamethylenediamine, piperazine, aminoethylpiperazine, 2,5-dimethyl-2,5-hexanediamine, 1,12-dodecanediamine, tris-3-aminopropylamine, 4,4'-diaminostilbene, 4,4'-diaminobenzanilide, 3,9,'-dimethyl-4,4'-diaminobiphenyl, or any combination thereof and the like.

The curing agents are employed in amounts which will effectively cure the composition; however, these amounts will depend upon the particular polyglycidyl amine and curing agent employed. Generally, suitable amounts include, for example, from about 0.95:1 to about 1.2:1 equivalents of curing agent per equivalent of polyglycidyl amine.

The monoglycidyl amines containing one or more mesogenic moieties of the present invention can be employed as reactive diluents for the polyglycidyl amines of the present invention as well as for polyglycidyl amines substantially free of mesogenic moieties, or epoxy resins. For polyglycidyl amines free of mesogenic moieties, the monoglycidyl amines provide a means of incorporating mesogenic moieties into the composition so as to enhance one or more properties when cured.

The mesogenic polyglycidyl amines of the present invention can also be employed for the purpose of improving the properties of epoxy resins substantially free of mesogenic moieties. Generally, suitable amounts of mesogenic polyglycidyl amines are from about 1 to about 99, more suitably from about 10 to about 80, most suitably from about 10 to about 50 weight percent based on the total weight of the combined resins. Representative of the epoxy resins free of mesogenic moieties include, for example, the diglycidyl ethers of resorcinol, bisphenol A, 4,4'-dihydroxydiphenylmethane, 3,3',5,5'-tetrabromobisphenol A, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3',5,5'-tetrachlorobisphenol A, 3,31-dimethoxybisphenol A; the triglycidyl ether of tris(hydroxyphenyl)methane; the polyglycidyl ether of a phenol or substituted phenolaldehyde condensation product (novolac); the polyglycidyl ether of a dicyclopentadiene or an oligomer thereof and phenol condensation product; the advancement reaction products of the aforesaid di- and polyglycidyl ethers with aromatic di- or polyhydroxyl- or carboxylic acid- containing compounds including, for example, bisphenol A (4,4'-isopropylidenediphenol), o-, m-, p-dihydroxybenzene, 2,4-dimethylresorcinol, 4-chlororesorcinol, tetramethylhydroquinone, 1,1-bis(4-hydroxyphenyl)ethane, 1,1-bis(4-hydroxyphenyl)-1-phenylethane, 4,4'-dihydroxydiphenyl ether, 3,3 ',5,5'-tetramethyldihydroxydiphenyl ether, 3,3',5,5'-dichlorodihydroxydiphenyl ether, 4,4'-bis(p-hydroxyphenyl isopropyl)diphenyl ether, 4,4'-bis(p-hydroxyphenoxy)benzene, 4,4'-bis(p-hydroxyphenoxy)diphenyl ether, 4,4'-bis(4(4-hydroxyphenoxy)-phenyl sulfone)diphenyl ether, 4,4'-dihydroxydiphenyl sulfone, 4,4'-dihydroxydiphenyl sulfide, 4,4'-dihydroxydiphenyl disulfide, 2,2'-dihydroxydiphenyl sulfone, 4,4'-dihydroxydiphenyl methane, 1,1-bis(p-hydroxyphenyl)cyclohexane, 4,4'-dihydroxybenzophenone, phloroglucinol, pyrogallol, 2,2',5,51-tetrahydroxydiphenyl sulfone, tris(hydroxyphenyl)methane, dicyclopentadiene diphenol, tricyclopentadiene diphenol; mixtures thereof and the like.

Before and/or during processing and/or curing of the polyglycidyl amine compositions into a part, electric or magnetic fields or shear stresses can be applied for the purpose of orienting the liquid crystal moieties contained or developed therein which in effect improves the mechanical properties. As specific examples of these methods, Finkelmann, et al, *Macromol. Chem.*, 180, 803-806 (March 1979) induced orientation in thermotropic methacrylate copolymers containing mesogenic side chain groups decoupled from the main chain via flexible spacers in an electric field. Orientation of mesogenic side chain groups decoupled from the polymer main chain via flexible spacers in a magnetic field has been demonstrated by Roth and Krueeke, *Macromol. Chem.*, 187, 2655-2662 (November 1986). Magnetic field induced orientation of mesogenic main chain containing polymers has been demonstrated by Moore, et al, *ACS Polymeric Material Sciences and Engineering*, 52, 84-86 (April-May 1985). Magnetic and electric field orientation of low molecular weight mesogenic compounds is discussed by W. R. Krigbaum in *Polymer Liquid Crystals*, pages 275-309 (1982) published by Academic Press, Inc. All of the above are incorporated herein by reference in their entirety.

In addition to orientation by electric or magnetic fields, polymeric mesophases can be oriented by shear forces which are induced by drawing and/or flow through dies, orefices, and mold gates. A general discussion for orientation of thermotropic liquid crystal polymers by this method is given by S. K. Garg and S. Kenig in *High Modulus Polymers*, pages 71-103 (1988) published by Marcel Dekker, Inc. For the mesomorphic systems based on the polyglycidyl amine compositions, this shear orientation can be produced by processing methods such as injection molding, extrusion, pultrusion, filament winding, filming and prepreging.

The mesogenic polyglycidyl amines of the present invention can be blended with other materials such as solvents or diluents, fillers, pigments, dyes, flow modifiers, thickeners, reinforcing agents, mold release agents, wetting agents, stabilizers, fire retardant agents, surfactants, combinations thereof and the like.

These additives are added in functionally equivalent amounts. e.g., the pigments and/or dyes are added in quantities which will provide the composition with the desired color; however, they are suitably employed in amounts of from about zero to about 20, more suitably from about 0.5 to about 5, most suitably from about 0.5 to about 3 percent by weight based upon the weight of the total blended composition.

Solvents or diluents which can be employed herein include, for example, hydrocarbons, ketones, glycol ethers, aliphatic ethers, cyclic ethers, amines, amides, combinations thereof and the like. Particularly suitable solvents or diluents include, for example, toluene, benzene, xylene, methyl ethyl ketone, methyl isobutyl ketone, diethylene glycol methyl ether, dipropylene glycol methyl ether, dimethylformamide, N-methylpyrrolidinone, tetrahydrofuran, propylene glycol methyl ether, combinations thereof and the like.

The modifiers such as thickeners, flow modifiers and the like can be suitably employed in amounts of from zero to about 10, more suitable from about 0.5 to about 6, most suitably from about 0.5 to about 4 percent by weight based upon the weight of the total composition.

Reinforcing materials which can be employed herein include natural and synthetic fibers in the form of woven fabric, mats, monofilament, multifilament, unidirectional fibers, rovings, random fibers or filaments, inorganic fillers or whiskers, hollow spheres, and the like. Suitable reinforcing materials include, glass, ceramics. nylon, rayon, cotton, aramid, graphite, polyalkylene terephthalates, polyethylene, polypropylene, polyamines, combinations thereof and the like.

Suitable fillers which can be employed herein include, for example, inorganic oxides, ceramic microspheres, plastic microspheres, glass microspheres, inorganic whiskers, $CaCO_3$, combinations thereof and the like.

The fillers can be employed in amounts suitable from about zero to about 95, more suitably from about 10 to about 80, most suitable from about 40 to about 60 percent by weight based upon the weight of the total composition.

The following examples are illustrative of the present invention, but are not to be construed as to limiting its scope in any manner.

EXAMPLE 1

A. Synthesis of 4,4'-Dinitrostilbene

Nitrobenzyl chloride (74.5 grams, 0.434 mole), ethanol (587 milliliters) and acetone (25.22 grams, 0.434 mole) are added to a reactor and stirred under a nitrogen atmosphere with cooling to provide a 22° C. mixture. Dropwise addition of a solution of sodium hydroxide (19.11 grams, 0.478 mole) in ethanol (352 milliliters) commences and is completed over the next 25 minutes inducing a reaction temperature increase to 34° C. After an additional three minutes, heating commences and a reaction temperature of 77° C. at reflux is achieved 12 minutes later. After an additional 6 hour of refluxing, the reactor contents are added to deionized water (3.5 liters) followed by acidification of the product slurry with hydrochloric acid to a pH of 2 with mixing. The resultant precipitated product is recovered by filtration, washed with deionized water (250 milliliters), then added to dimethylsulfoxide (450 milliliters) and heated to 140° C. to provide a solution. Recrystallization is accomplished by gradual cooling and holding of the dimethylsulfoxide solution at 5° C. overnight followed by filtration to recover the crystalline precipitate. A second recrystallization is completed by adding the wet filter cake to acetone (150 milliliters) followed by heating to a boil. Recrystallization is accomplished by gradual cooling and holding of the acetone solution at 5° C. overnight followed by filtration to recover the crystalline precipitate. The recovered filter cake is dried in a vacuum oven at 110° C. and 5 mm Hg to a constant weight of 39.2 grams. The product is recovered as brilliant yellow colored needlelike crystals. Additional solids precipitated from the dimethylsulfoxide mother liquor from the initial recrystallization, but no attempt is made to recover and process this material. Fourie transform infrared spectrophotometric analysis of a potassium chloride pellet of the product confirms the product structure: 1503 and 1337 cm$^{-1}$ conjugated nitro group absorbance, with the 1503 cm$^{-1}$ conjugated nitro group absorbance masking the aromatic ring absorbance. Proton nuclear magnetic resonance spectroscopy further confirms the product structure.

B. Synthesis of 4,4'-Diaminostilbene

A portion (20.27 grams, 0.075 mole) of 4,4'-dinitrostilbene from A above, concentrated hydrochloric acid (150 milliliters) and ethanol (300 milliliters) are added to a beaker and heated to provide a 60° C. stirred solution. Over the next eight hour period, 325 mesh powdered iron is added to the reaction mixture in aliquots until a total of 33-51 grams (0.60 mole) has been added. After completion of the iron addition, the mixture is heated for 16 hours at 60° C. then diluted with ethanol (250 milliliters) and deionized water (250 milliliters). After cooling to 25° C., the product is filtered. The resultant solution is treated with 50% aqueous sodium hydroxide sufficient to induce precipitation of a pale tan colored product which is recovered by filtration. The recovered filter cake is washed with deionized water (500 milliliters) then dried in a vacuum oven at 100° C. and 2 mm Hg to a constant weight of 11.3 grams. The product is recovered as a pale tan colored solid. Fourier transform infrared spectrophotometric analysis of a potassium chloride pellet of the product confirms the product structure: Disappearance of the absorbances observed for the conjugated nitro group, appearance of —NH$_2$ stretching absorbances at 3436 (3462 shoulder) and 3356 (3376 shoulder) cm$^{-1}$, a —NH$_2$ bending absorbance at 1616 cm$^{-1}$ (1603 cm$^{-1}$ shoulder due to aromatic ring absorbance), an out-of-plane C—H deformation at 970 cm$^{-1}$ due to the trans substituted ethylene group and a C—H out-of-plane bending vibration at 832 cm$^{-1}$ due to the paradisubstituted aromatic rings. Proton nuclear magnetic resonance spectroscopy further confirms the product structure.

C. Synthesis of 4,4'-Diacetamidostilbene 4,4'-Diaminostilbene (8.9 grams, 0.0847 —NH$_2$ equivalent) from B above, is ground to a fine powder and added to a beaker containing stirred, 90° C. deionized water (1500 milliliters). After two minutes, aqueous 36.5% hydrochloric acid (8.47 grams, 0.0847 mole) is added to the stirred, 90° C. suspension. The solution which formed within five minutes is cooled to 60° C. Acetic anhydride (10.61 grams, 0.1039 mole) is added to the stirred solution and mixed therein for 30 seconds before addition of an aqueous sodium acetate solution (prepared by dissolution of anhydrous sodium acetate [1 3. 89 grams, 0. 1693 mole] in deionized water [4 1.7 grams]). After thoroughly stirring the white slurry, it is maintained at 4° C. for 16 hours, followed by filtration to remove the precipitated product. The recovered filter cake is washed with two portions (250 milliliters) of deionized water then dried in a vacuum oven at 80° C. and 2 mm Hg to a constant weight of 11.44 grams. The product is recovered as a tan colored crystalline powder. Fourier transform infrared spectrophotometric analysis of a potassium chloride pellet of the product confirms the product structure: disappearance of the absorbances observed for the —NH$_2$ group, appearance of solid state >NH stretching absorbances at 3309 (3396 and 3190 shoulders) cm$^{-1}$, a solid state amide I carbonyl stretching absorbance at 1669 cm$^{-1}$, a solid state amide II carbonyl stretching absorbance at 1516 cm$^{-1}$ (masking the aromatic ring absorbance), an out-of-plane C—H deformation at 959 cm$^{-1}$ due to the trans substituted ethylene group and a C—H out-of-plane bending vibration at 832 cm$^{-1}$ due to the para-disubstituted aromatic rings. Proton nuclear magnetic resonance spectroscopy further confirms the product structure.

D. Synthesis of N,N'-dimethyl-4,4'-diacetamidostilbene 4,4'-Diacetamidostilbene (10.35 grams, 0.0694 —N—H—CO— equivalent) from C above, tetra-n-butylammonium hydrogen sulfate (2.36 grams, 0.0069 mole), powdered 99% sodium hydroxide (9.71 grams, 0.2429 mole), anhydrous powdered potassium carbonate (19.42 grams, 0.1405 mole) and benzene (200 milliliters) are added to a reactor and stirred under a nitrogen atmosphere to provide a 21° C. mixture. After two minutes, dimethyl sulfate (13.13 grams, 0.1041 mole) is added to the stirred mixture then heating is initiated. After nine minutes, the mixture reached a reflux temperature of 81° C. After 363 minutes at the 81° C. reflux, Fourier transform infrared spectrophotometric analysis of a sample of the organic layer of the reaction mixture revealed that full conversion to the N,N'-dimethyl derivative had occurred. Sixteen minutes later, additional benzene (200 milliliters) and deionized water (100 grams) are added to the reactor and thoroughly mixed with the reaction mixture. The reactor contents are added to a separatory funnel and the aqueous layer which separated is removed and discarded. The benzene solution is washed with two portions of deionized water (100 milliliters), dried over anhydrous sodium sulfate, then rotary evaporated to remove solvent. The recovered powder is then dried in a vacuum oven at 80° C. and 2 mm Hg to a constant weight of 7.55 grams. The product is recovered as a white crystalline powder. Fourier transform infrared spectrophotometric analysis of a film of the product on a potassium chloride plate confirms the product structure: disappearance of the absorbances observed for the secondary amide group, appearance of a tertiary amide carbonyl stretching absorbance at 1656 cm$^{-1}$, a C—H stretching absorbance at 2878 cm$^{-1}$ due to the >N—CH$_3$ groups, an out-of-plane C—H deformation at 972 cm$^{-1}$ due to the trans substituted ethylene group and a C—H out-of-plane bending vibration at 846 (839 shoulder) cm$^{-1}$ due to the para-disubstituted aromatic rings. Proton nuclear magnetic resonance spectroscopy further confirms the product structure.

E. Hydrolysis of N,N'-dimethyl-4,4'-diacetamidostilbene

N,N'-dimethyl-4,4'-diacetamidostilbene (7.50 grams, 0.0460 —N—(CH3)—CO— equivalent) from D above is added to a reactor and dissolved with stirring under a nitrogen atmosphere in ethanol (170 milliliters). Concentrated hydrochloric acid (9.07 grams, 0.0920 mole) is added to the resultant 25° C. solution inducing a maximum exotherm of 34° C. one minute later. The stirred reaction mixture is allowed to cool to 25° C. over the next forty eight minutes then heating to 50° C. commences. After eighty nine minutes at 50° C., additional concentrated hydrochloric acid (9.07 grams) is added to the solution. After an additional 149 minutes at 50° C., additional concentrated hydrochloric acid (9.07 grams) is added to the solution and heating to 75° C. commences. After seventy six minutes at 75° C., additional concentrated hydrochloric acid (18.14 grams) is added to the solution. After 22.5 hours at the 75° C. temperature, Fourier transform infrared spectrophotometric analysis of a sample of the solution as a neat film on a potassium chloride plate revealed that complete hydrolysis of the amide linkages had occurred concurrent with the formation of the amine hydrochloride salt of the diamine thus produced: disappearance of the tertiary amide carbonyl stretching absorbance, appearance of —NH$_3$+ stretching absorbances at 2665 and 2446 cm$^{-1}$, a NH$_3$+ bending absorbance at 1603 cm$^{-1}$ (masking the aromatic ring absorbance). At this time, deionized water (500 grams) is added to the reactor and thoroughly mixed with the reaction mixture. The reactor contents are cooled to 25° C. then 50% aqueous sodium hydroxide is added with mixing to a pH of 9 followed by filtration of the precipitated product. The recovered filter cake is washed with two portions (100 milliliters) of deionized water then dried in a vacuum oven at 80° C. and 2 mm Hg to a constant weight of 5.02 grams. The product is recovered as a light yellow colored crystalline powder. Fourier transform infrared spectrophotometric analysis of a potassium bromide pellet of the product confirms the product structure: disappearance of the tertiary amide carbonyl stretching absorbance, appearance of a >NH stretching absorbance at 3416 (3389 shoulder) cm$^{-1}$. a C—H stretching absorbance at 2818 cm$^{-1}$ due to the >N—CH$_3$ groups, an out-of-plane C—H deformation at 965 cm$^{-1}$ due to the trans substituted ethylene group and a C—H out-of-plane bending vibration at 826 cm$^{-1}$ due to the paradisubstituted aromatic rings. Proton nuclear magnetic resonance spectroscopy further confirms the product structure.

F. Epoxidation of N,N'-dimethyl-4,4'-diaminostilbene

N,N'-dimethyl-4,4'-diaminostilbene (2.383 grams, 0.02 >NH equivalent) from E above, epichlorohydrin (7.402 grams, 0.08 mole) and ethylene glycol (0.991 gram, 0.0320 hydroxyl equivalent) are added to a reactor and heated to 50° C. with stirring under a nitrogen atmosphere. After 3 hours at the 50° C. temperature, cooling to 35° C. commenced. After seven minutes the 35° C. temperature is achieved and sodium hydroxide (0.952 gram, 0.0238 mole) dissolved in deionized water (1.04 grams, 52% of total solution) is added to the reactor. A maximum exotherm of 42° C. occurs within one minute with the reaction temperature reduced back to 35° C. within an additional minute via cooling of the reactor exterior. After an additional eighteen minutes at 35° C, the reaction mixture is recovered and rotary evaporated at 55° C. and 2 mm Hg final vacuum to remove residual epichlorohydrin. The solids remaining after rotary evaporation are thoroughly mixed with methylethylketone (100 milliliters) then extracted with deionized water (150 milliliters). The mixture is added to a separatory funnel and the aqueous layer which separated is removed and discarded. The methylethylketone solution is washed with two portions (50 milliliters) of deionized water, then rotary evaporated at 55° C. and 1 mm Hg final vacuum for 90 minutes. The product is recovered as a light yellow colored crystalline powder with an epoxide equivalent weight (EEW) of 192.19 (corrected for titrated contribution of amine nitrogen).

EXAMPLE 2

Characterization of the Diglycidyl Amine of N,N'-dimethyl-4,4'-diaminostilbene by Optical Microscopy and Differential Scanning Calorimetry A portion (12.50 milligrams) of the diglycidyl amine of N,N'-dimethyl-4,4'-diaminostilbene from Example 1-F is analyzed by differential scanning calorimetry using a heating rate of 10° C. per minute and a temperature range of 0° to 130° C. under a stream of nitrogen flowing at 35 cubic centimeters per minute. The results are given in Table I.

TABLE I

| Cycle Designation | Observed Transition Temperatures (°C.) midpoint/range | Enthalpy (j/g) | Comments |
| --- | --- | --- | --- |
| First heating (0 to 130° C.) | 33/33–46 | 0.78 | single endotherm |
|  | 75 and 103/46–112 | 43.8 | endotherm with shoulder at 75° C. |
| First cooling (130 to 0° C. | 55.5/43–67 | 33.8 | single exotherm |

Analysis of the diglycidyl amine of N,N'-dimethyl-4,4'-diaminostilbene via crosspolarized light microscopy is completed using a microscope equipped with a programmable hot stage using a heating rate of 100° C. per minute. The results are given in Table II.

TABLE II

| Cycle Designation | Observed Transition Temperatures (°C.) | Comments |
| --- | --- | --- |
| First heating (30 to 135° C.) | 30 | Birefringent crystalline solid. |
|  | 102 | Melting observed. |
|  | 103 | Crystalline dispersion. |
|  | 119 | Isotropization. |
| First cooling (135 to 30° C.) | 135 | Isotropic fluid. |
|  | 74 | Crystallization begins. |
|  | 64 | Birefringent crystalline solid. |

EXAMPLE 3

Copolymerization of Diglycidyl Amine of N,N'-dimethyl-4,4'-diaminostilbene and N,N'-dimethyl-4,4'-diaminostilbene and Analysis via Optical Microscopy and Differential Scanning Calorimetry A portion (0.2485 grams) of the diglycidyl amine of N,N'-dimethyl-4,4'-diaminostilbene from Example 1-F above is combined with an equivalent amount (0.1541 grams) of N,N'-dimethyl-4,4'-diaminostibene from Example 1-E above. These compounds are ground together to form a fine, homogeneous powder. A sample of this mixture is placed on a hot stage which has been heated to 100° C. and then observed via optical microscopy under crosspolarized light at 70× magnification. At the 100° C. temperature, a birefringent crystalline dispersion occurred in less than one minute. Heating to 140° C. is then resumed and complete isotropization occurs at 132° C. After ten minutes at 140° C, the resin exhibits opacity at the edges of the coverslip and small birefringent domains throughout. After an additional twelve minutes at 140° C., the resin is still fluid and shear applied to the resin aligns the birefringent domains in a direction perpendicular to the direction of the shear. After an additional sixteen minutes at 140° C., the resin becomes an opaque, birefringent solid with a nematic texture. Further heating to 180° C. reduces the number of nematic domains present with oriented domains still observable. After cooling to 25° C., a highly birefringent, opaque solid with a nematic texture is observed.

A second sample of the mixture is placed on a hot stage which has been heated to 140° C. and then observed via optical microscopy under crosspolarized light at 70× magnification. At the 140° C. temperature, an isotropic fluid containing a trace of birefringent domains is observed after three minutes. At this time, cooling at a rate of 10° C. per minute is initiated. Once 120° C. is achieved, this temperature is held. After eleven minutes at 120° C. the resin still appears as an isotropic fluid containing a trace of birefringent domains. After an additional six minutes at 120° C., a second birefringent phase forms and the resin becomes opaque and viscous. At this time, application of shear to the resin induces alignment of some of the birefringent domains in the direction of the shear. After an additional sixteen minutes at 120° C., the resin becomes an opaque, birefringent solid with a nematic texture with a diminished number of oriented domains observable. After an additional twenty seven minutes at 120° C., cooling to 25° C. commences to provide a highly birefringent, opaque solid with a nematic texture.

A third sample (10.10 milligrams) of the mixture is analyzed by differential scanning calorimetry using a heating rate of 10° C. per minute and a temperature range of 30° to 280° C. under a stream of nitrogen flowing at 35 cubic centimeters per minute.

TABLE III

| Cycle Designation | Observed Transition Temperatures (°C.) midpoint/range | Enthalpy (j/g) | Comments |
| --- | --- | --- | --- |
| First heating (30 to 280° C.) | 82/50–126 | 33.5 | single endotherm |
|  | 189/127–243 | 162.3 | broad exotherm |

EXAMPLE 4

Preparation of a Neat Resin Casting of the Diglycidyl Amine of N,N'-dimethyl-4,4'-diaminostilbene Cured with N,N'-dimethyl-4,4'-diaminostilbene and Analysis via Optical Microscopy and Differential Scanning Calorimetry.

The powder mixture of the diglycidyl amine of N,N'-dimethyl-4,4'-diaminostilbene and N,N'-dimethyl-4,4'-diaminostilbene remaining from Example 3 is transferred to an aluminum cup. The aluminum cup containing this mixture is placed in an oven which has been heated to 140° C. After one minute at 140° C., a partial melt is observed. After an additional nine minutes, a melt is obtained. At this time, the oven temperature is reduced to 120° C. After an additional seventeen minutes, the resin becomes viscous and immobile. After an additional fifteen minutes, the resin gelled to an opaque solid which is then held at the 120° C. temperature for an additional five hours and fifteen minutes. Thin sections of the demolded casting exhibited a high level of birefringence and a nematic texture when observed via optical light microscopy under crosspolarized light at 70× magnification.

Differential scanning calorimetry of a portion (25.0 milligrams) of the casting using a heating rate of 10° C. per minute and a temperature range of 30° to 240° C. under a stream of nitrogen flowing at 35 cubic centimeters per minute provided the results in Table IV.

TABLE IV

| Cycle Designation | Observed Transition Temperatures (°C.) midpoint/range | Enthalpy (j/g) | Comments |
|---|---|---|---|
| First heating (30 to 240° C.) | 183/165–196 | 3.2 | single endotherm |
| | 217/196–229 | 19.4 | single endotherm |

Analysis of a portion of the casting via crosspolarized light microscopy is completed using a microscope equipped with a programmable hot stage using a heating rate of 10° C. per minute. The results are given in Table V.

TABLE V

| Cycle Designation | Observed Transition Temperatures (°C.) | Comments |
|---|---|---|
| First heating (30 to 135° C.) | 30 | Solid |
| | 170 | First melting observed |
| | 178 | Isotropic liquid containing birefringent domains. |
| | 216 | Isotropization. |

EXAMPLE 5

A. Synthesis of 3,3′-Dimethyl-4,4′-diacetamidobiphenyl 3,3′-Dimethyl-4,4′-diaminobiphenyl (12.74 grams, 0.12 —NH$_2$ equivalent) is ground to a fine powder and added to a beaker containing stirred, 90° C. deionized water (1200 milliliters). After two minutes, aqueous 36.5% hydrochloric acid (12.00 grams, 0.12 mole) is added to the stirred, 90° C. suspension. The solution which formed in six minutes is cooled to 70° C. Acetic anhydride (15.04 grams, 0.473 mole) is added to the stirred solution and mixed therein for 20 seconds before addition of an aqueous sodium acetate solution (prepared by dissolution of anhydrous sodium acetate [19.69 grams, 0.24 mole]in deionized water [60.0 grams]). After thoroughly stirring the white slurry, it is maintained at 4° C. for 16 hours, followed by filtration to remove the precipitated product. The recovered filter cake is washed with two portions (150 milliliters) of deionized water then dried in a vacuum oven at 60° C. and 5 mm Hg to a constant weight of 16.92 grams. The product is recovered as a white crystalline powder. Fourier transform infrared spectrophotometric analysis of a potassium chloride pellet of the product confirms the product structure: disappearance of the absorbances observed for the —NH$_2$ group, appearance of solid state >NH stretching absorbances at 3283 (3183 slight shoulder) cm$^{-1}$, a solid state amide I carbonyl stretching absorbance at 1656 cm$^{-1}$, a solid state amide II carbonyl stretching absorbance at 1516 cm$^{-1}$ (masking the aromatic ring absorbance) and a C—H out-of-plane bending vibration at 819 cm$^{-1}$ due to the paradisubstituted aromatic rings. Proton nuclear magnetic resonance spectroscopy further confirms the product structure.

B. Synthesis of 3,3′-Dimethyl—N,N′-dimethyl-4,4′-diacetamidobiphenyl 3,3′-Dimethyl-4,4′-diacetamidobiphenyl (30.03 grams, 0.2027 —NH—CO— equivalent) prepared using the method of A above, tetra-n-butylammonium hydrogen sulfate (6.79 grams, 0.02 mole), powdered 99% sodium hydroxide (28.0 grams, 0.70 mole), anhydrous powdered potassium carbonate (56.0 grams, 0.4052 mole) and benzene (800 milliliters) are added to a reactor and stirred under a nitrogen atmosphere to provide a 21° C. mixture. After two minutes, dimethyl sulfate (37.84 grams. 0.30 mole) is added to the stirred mixture then heating is initiated. After eleven minutes, the mixture reached a reflux temperature of 81° C. After 208 minutes at the 81° C. reflux, Fourier transform infrared spectrophotometric analysis of a sample of the organic layer of the reaction mixture revealed that full conversion to the N,N′-dimethyl derivative had occurred. Sixteen minutes later, additional benzene (400 milliliters) and deionized water (300 grams) are added to the reactor and thoroughly mixed with the reaction mixture. The reactor contents are added to a separatory funnel and the aqueous layer which separated is removed and discarded. The benzene solution is washed with two portions of deionized water (200 milliliters), dried over anhydrous sodium sulfate, then rotary evaporated to remove solvent. The recovered powder is then dried in a vacuum oven at 50° C. and 12 mm Hg to a constant weight of 32.61 grams. The product is recovered as a white crystalline powder. Fourier transform infrared spectrophotometric analysis of a film of the product on a potassium chloride plate confirms the product structure: disappearance of the absorbances observed for the secondary amide group, appearance of a tertiary amide carbonyl stretching absorbance at 1663 cm$^{-1}$, a C—H stretching absorbance at 2878 cm$^{-1}$ due to the >N—CH$_3$ groups and a C—H out-of-plane bending vibration at 826 cm$^{-1}$ due to the para-disubstituted aromatic rings. Proton nuclear magnetic resonance spectroscopy further confirms the product structure.

C. Hydrolysis of 3,3′-Dimethyl—N,N′-dimethyl-4,4′-diacetamidobiphenyl 3,3′-Dimethyl—N,N′-dimethyl-4,4′-diacetamidobiphenyl (32.44 grams, 0.20 —N—(CH$_3$)—CO— equivalent) from B above is added to a reactor and dissolved with stirring under a nitrogen atmosphere in ethanol (600 milliliters). Concentrated hydrochloric acid (157.87 grams, 1.60 moles) is added to the resultant 22° C. solution inducing a maximum exotherm of 43° C. two minutes later. The stirred reaction mixture is heated to 75° C. over the next seven minutes. After 23 hours at 75° C., heating to a 85° C. reflux commences. After 96 hours at the 86° C. temperature, Fourier transform infrared spectrophotometric analysis of a sample of the solution as a neat film on a potassium chloride plate revealed that complete hydrolysis of the amide linkages had occurred concurrent with the formation of the amine hydrochloride salt of the diamine thus produced: disappearance of the tertiary amide carbonyl stretching absorbance, appearance of —NH$_3$+ stretching absorbances at 2659 and 2446 cm$^{-1}$, a NH$_3$+ bending absorbance at 1609 cm$^{-1}$ (masking the aromatic ring absorbance). At this time, deionized water (400 grams) is added to the disubstituted reactor and thoroughly mixed with the reaction mixture. The reactor contents are cooled to 25° C. then 50% aqueous sodium hydroxide is added with mixing to a pH of 9 followed by filtration of the precipitated product. The recovered filter cake is washed with two portions (100 milliliters) of deionized water then dried in a vacuum oven at 40° C. and 10 mm Hg to a constant weight of 22.01 grams. The product is recovered as a white crystalline powder. Fourier transform infrared spectrophotometric analysis of a potassium bromide pellet of the product confirms the product structure: disappearance of the tertiary amide carbonyl stretching absorbance, appearance of a >NH stretching absorbance at 3429 (3369 shoulder) cm$^{-1}$, a C—H stretching absorbance at 2818 cm$^{-1}$ due to the >N—CH$_3$ groups and a C—H out-of-plane bending vibration at 806 cm$^{-1}$ due to the para-disubstituted aromatic rings. Proton nuclear magnetic resonance spectroscopy further confirms the product structure.

D. Epoxidation of 3,3'-Dimethyl—N,N'-dimethyl-4,4'-diaminobiphenyl 3,3'-Dimethyl—N,N'-dimethyl-4,4'-diaminobiphenyl (6.01 grams, 0.05 >NH equivalent) from C above, epichlorohydrin (18.51 grams, 0.20 mole) and ethylene glycol (2.48 gram, 0.08 hydroxyl equivalent) are added to a reactor and heated to 50° C. with stirring under a nitrogen atmosphere. After 3 hours at the 50° C. temperature, cooling to 35° C. commenced. After ten minutes the 35° C. temperature is achieved and sodium hydroxide (2.38 grams, 0.0595 mole) dissolved in deionized water (2.58 grams, 52% of total solution) is added dropwise to the reactor over a thirteen minute period and so as to maintain a 35° to 38° C. reaction temperature. After an additional fifteen minutes at 35° C., the reaction mixture is recovered and rotary evaporated at 55° C. and 2 mm Hg final vacuum to remove residual epichlorohydrin. The solids remaining after rotary evaporation are thoroughly mixed with methylethylketone (250 milliliters) then extracted with deionized water (100 milliliters). The mixture is added to a separatory funnel and the aqueous layer which separated is removed and discarded. The methylethylketone solution is washed with two portions (75 milliliters) of deionized water, then rotary evaporated at 50° C. and I mm Hg final vacuum for 90 minutes. The product is recovered as a tacky clear amber solid with an epoxide equivalent weight (EEW) of 188.73 (corrected for titrated contribution of amine nitrogen).

What is claimed is:

1. A phenoxy resin prepared by reacting (A) one or more polyglycidyl amines containing one or more mesogenic moieties, said polyglycidyl amines being those represented by the following Formulas I, III, V or VI

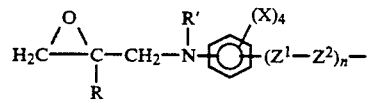

Formula I

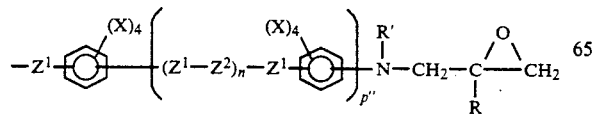

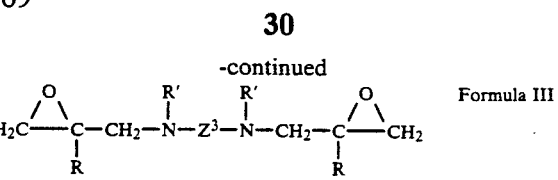

Formula III

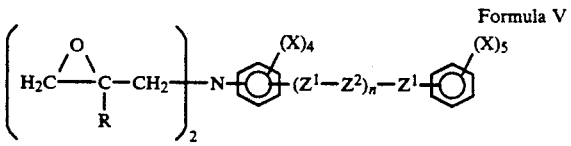

Formula V

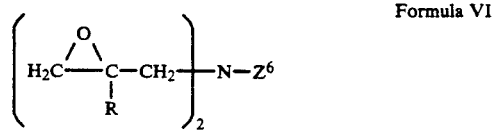

Formula VI wherein at least about 80 percent of the —(Z$^1$—Z$^2$)$_n$—Z$^1$— linkages and the glycidyl amine groups are in the para position with respect to each other; each R and R$^1$ is independently hydrogen or an aliphatic hydrocarbon group having from 1 to about 4 carbon atoms; each R' is independently a hydrocarbyl group having from 1 to about 12 carbon atoms; each X is independently hydrogen, a hydrocarbyl or hydrocarbyloxy group having suitably from 1 to about 12 carbon atoms, a halogen atom, —NO$_2$, or —C≡N; X$^1$ is a divalent hydrocarbyl group having from 1 to about 10 carbon atoms which can contain one or more heteroatoms selected from N, O or S and may be saturated or unsaturated; each Z$^1$ is independently a direct single bond, —CR$^1$=CR$^1$—, —CR$^1$=CR$^1$—CR$^1$=CR$^1$—, —CR$^1$=N—N=CR$^1$—, —CR$^1$=CR$^1$—CO—O—(CHR$^1$)$_{p'}$—, —CR$^1$=CR$^1$—O—CO—(CHR$^1$)$_{p'}$—, —(CHR$^1$)$_{p'}$—O—CO—CR$^1$=CR$^1$—, —(CHR$^1$)$_{p'}$—CO—O—CR$^1$=CR$^1$—, —CR$^1$=CR$^1$—CO—O—, —O—CO—CR$^1$=CR$^1$—, —CO—NR$^1$—, —NR$^1$—CO—, —CO—NR$^1$—NR$^1$—CO—, —C≡C—, —C≡C—C≡C—, —CO—S—, —S—CO—, —CR$^1$=N—, —N=CR$^1$—, —O—CO—, —CO—O—, —CR$^1$=C-R$^1$—CO—, —CO—CR$^1$=CR$^1$—, —CR$^1$=CR$^1$—O—CO—, —CO—O—CR$^1$=CR$^1$—, —CH$_2$—CH$_2$—CO—O—, —O—CO—CH$_2$—CH$_2$—, —N=N—,

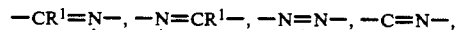

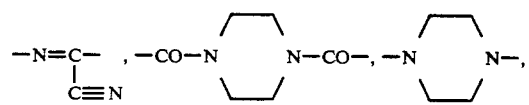

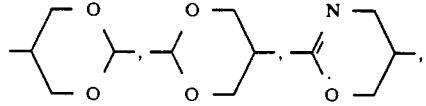

-continued

[structures: oxazine-like ring with (CH₂)ₚ; dibenzofuran-like —(Z')ₙ'—...—(Z')ₙ'—]

—CR¹=C—, —C=CR¹—, —CR¹=C—, —C=CR¹—
     |        |         |        |
     Cl       Cl        C≡N      C≡N

[N-methylbenzimidazole with (Z')ₙ']

—(Z')ₙ'—⟨cyclohexyl⟩—(Z')ₙ'—,

[biphenylene with (Z')ₙ' groups]

—(Z')ₙ'—⟨CHR¹ cyclohexyl⟩—(Z')ₙ'—,

[benzoxazole-benzo fused, benzothiazole-benzo fused structures]

—(Z')ₙ'—⟨cyclohexenyl⟩—(Z')ₙ'—, —(Z')ₙ'—⟨cyclohexenyl⟩—(Z')ₙ'—,

[oxazole/benzoxazole and thiazole/benzothiazole fused structures]

—(Z')ₙ'—⟨cyclohexenyl⟩—(Z')ₙ'—, $Z^2$ is a group represented by a cyclic or bicyclic ring system containing from 5 to about 12 carbon atoms and may be cycloaliphatic, polycycloaliphatic, aromatic or a combination thereof; $Z^3$ is —Z'ₙ'—⟨quinoline⟩—(Z')ₙ'—,

[phenyl-(X)₄-CHR¹-cyclohexyl]

—(Z')ₙ'—⟨isoquinoline⟩—(Z')ₙ'—,

[cyclohexyl-CHR¹-Z⁴-phenyl-(X)₄]

—(Z')ₙ'—⟨furan⟩—(Z')ₙ'—,

[cyclohexyl-CHR¹-Z⁴-naphthyl], or

—(Z')ₙ'—⟨fluorene-like⟩—(Z')ₙ'—,

[biphenyl with (X)₃ and (X¹)ₙ' substituents]

—(Z')ₙ'—⟨phenanthrene-like⟩—(Z')ₙ'—, $Z^4$ is —CO—O—, —O—CO—, —NR¹—CO— or —CO—NR¹—; $Z^6$ is —(Z')ₙ'—⟨thiophene⟩—(Z')ₙ'—, —(Z')ₙ'—⟨N-methylbenzimidazole⟩,

[phenyl-(X)₄-CHR¹-cyclohexyl],

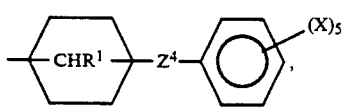
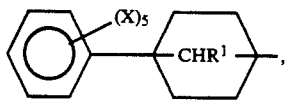
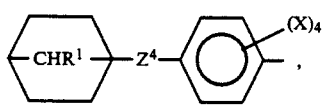
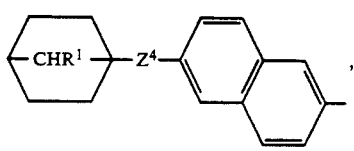
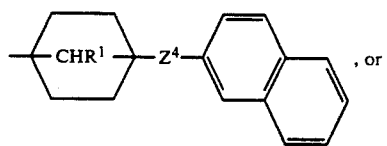
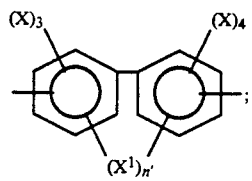
n is zero to 2; n' is zero or 1; p' is 1 or 2; p" has a value of zero to 100; and each Z' is independently a —CO—, —O—CO—, —CO—O—, —CO—NR$^1$—, or —NR$^1$—CO— group; with
(B) at least one compound having an average of more than one active hydrogen atom per molecule; wherein components (A) and (B) are employed in quantities which provide a ratio of active hydrogen atoms per epoxide group of from about 0.96:1 to about 1.05:1.
* * * * *